United States Patent
Zhang

(10) Patent No.: US 9,555,055 B2
(45) Date of Patent: Jan. 31, 2017

(54) USE OF ALBIFLORIN AND METABOLITES THEREOF

(76) Inventor: Zuoguang Zhang, Beijing (CN)

(*) Notice: Subject to any disclaimer, the term of this patent is extended or adjusted under 35 U.S.C. 154(b) by 401 days.

(21) Appl. No.: 13/989,524

(22) PCT Filed: Nov. 9, 2011

(86) PCT No.: PCT/CN2011/081984
§ 371 (c)(1),
(2), (4) Date: Aug. 5, 2013

(87) PCT Pub. No.: WO2012/068958
PCT Pub. Date: May 31, 2012

(65) Prior Publication Data
US 2013/0316966 A1 Nov. 28, 2013

(30) Foreign Application Priority Data
Nov. 25, 2010 (CN) .......................... 2010 1 0558722

(51) Int. Cl.
*A61K 31/7048* (2006.01)
*A61K 31/365* (2006.01)
*A61K 36/65* (2006.01)

(52) U.S. Cl.
CPC .......... *A61K 31/7048* (2013.01); *A23L 33/105* (2016.08); *A61K 31/365* (2013.01); *A61K 36/65* (2013.01)

(58) Field of Classification Search
None
See application file for complete search history.

(56) References Cited

U.S. PATENT DOCUMENTS

2003/0232102 A1* 12/2003 Zhao .......................... 424/778
2006/0198872 A1* 9/2006 Ikonte et al. ................. 424/439

FOREIGN PATENT DOCUMENTS

| CN | 1833668 A | 9/2006 |
| CN | 101062128 A | 11/2010 |
| CN | 102125575 A | 7/2011 |
| WO | WO 2007/038610 A2 * | 4/2007 |
| WO | WO-2010/133015 A1 | 11/2010 |

OTHER PUBLICATIONS

Mohler, Hans, Journal of Receptors and Signal Transduction, "GABA A Receptors in Central Nervous System Disease: Anxiety, Epilepsy, and Insomnia", 2006, vol. 26, pp. 731-740.*
"International Application No. PCT/CN2011/081984, International Search Report (with English translation) mailed Feb. 23, 2012", (Feb. 23, 2012), 11 pgs.
Wang, Qiao, et al., "HPLC Determination of albiflorin, paeoniflorin, and benzoylpaeoniflorin in total glucoside of paeony capsule", Chinese Traditional and Herbal Drugs, 2005, 36(11), 1630-1632, (2005), 1630-1632.
Yasui, Toshiyuki, et al., "Changes in circulating cytokine levels in midlife women with psychological symptoms with selective serotonin reuptake inhibitor and Japanese traditional medicine", Maturitas, 2009, 62(2), 146-152, (2009), 146-152.
Zhang, An-Ping, et al., "Effects of total glucosides of paeony on sleep-waking rhythm in rats", Chinese Pharmacological Bulletin, 1993, 9(6) 454-457, (1993), 454-457.

* cited by examiner

*Primary Examiner* — Shaojia Anna Jiang
*Assistant Examiner* — Bahar Craigo
(74) *Attorney, Agent, or Firm* — Schwegman Lundberg & Woessner, P.A.

(57) ABSTRACT

Disclosed is a use of albiflorin or a metabolite thereof in preparation of antianxiety and sleep disorder improving drugs or health-care food. Tests prove that albiflorin has significant antianxiety effects and sleep disorder improving effects achieved by prolonging SWS and low the toxic side effects, thus being a safety monomer compound capable of effectively treating anxiety and sleep disorder.

4 Claims, No Drawings

USE OF ALBIFLORIN AND METABOLITES THEREOF

PRIORITY CLAIM TO RELATED APPLICATIONS

This application is a national stage application under 35 U.S.C. §371 of PCT/CN2011/081984, filed Nov. 9, 2011, and published as WO 2012/068958 A1 on May 31, 2012, which claims priority to Chinese Application No. 201010558722.0, filed Nov. 25, 2010, which applications and publication are incorporated by reference as if reproduced herein and made a part hereof in their entirety, and the benefit of priority of each of which is claimed herein.

FIELD OF THE INVENTION

The present invention relates to a use of albiflorin or a metabolite of albiflorin in the preparation of a medicament or a health-care food for preventing, ameliorating and/or treating anxiety and sleep disorder.

BACKGROUND OF THE INVENTION

In modern society, due to the increasing competition and the accelerated pace of life, more and more people suffer from anxiety and sleep disorder. The function of current sedative hypnotics and anti-anxiety drugs (such as the benzodiazepine class) is characterized by making insomniacs fall asleep quickly. Although the time of light sleep may be prolonged, two important kinds of sleep, slow-wave sleep (SWS) and rapid eye movement sleep (REMS), are damaged in varying degrees. Accordingly, the sleeping quality has not been really improved, and the phenomena of dizziness, fatigue, drowsiness, inattention and the like occur inevitably. Repeated administration may result in psychological and physical dependence. A new generation of anti-anxiety, sedative hypnotics (such as buspirone) has made much progress in improving the sleeping quality, and without obvious addiction. However, after administration, side effects of dizziness, headache, and gastrointestinal disorders may occur. Therefore, it is necessary to continue to seek and develop new medicaments for the treatment of anxiety and sleep disorder.

Albiflorin is a natural active substance categorized as monoterpene, with a molecular formula of $C_{23}H_{28}O_{11}$ and a molecular weight of 480.46, and the molecular structure thereof is shown in Formula I. It is originated from the root of *Paeonia lactiflora* Pall, *Paeonia veitchii* Lynch or *P. suffrsticosa* Andrz of Ranunculaceae plants.

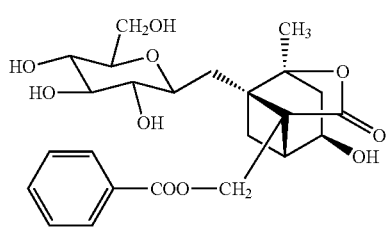

(I)

Albiflorin has a cyclic structure of lactone, but without a hemiacetal structure. It is converted under anaerobic conditions into two products, paeonilactone A and paeonilactone B, respectively. The structures of paeonilactone A and B are shown as Formula (II) and Formula (III), respectively:

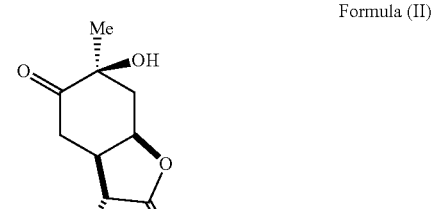

Formula (II)

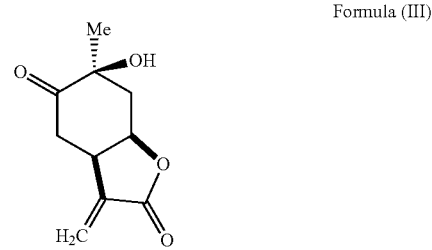

Formula (III)

Modern pharmacological studies indicate that Albiflorin has analgesic, anticonvulsant effects, immune system-related effects, smooth muscle-related effects, anti-inflammatory effect, effects against pathogenic microorganisms, and liver protection effect. Clinically speaking, it is mainly used for anti-epilepsia, analgesia, drug abuse rehabilitation, nausea-stopping, the treatment of rheumatoid arthritis, the treatment of bacillary dysentery and enteritis, the treatment of viral hepatitis, the treatment of age-related diseases, the resistance to barium sulfate flocculation and mucus dissolution.

As stated in the prior art (Anping, ZHANG et al., Effects of total glucosides of paeony on sleep-waking rhythm in rats, Chinese Pharmacological Bulletin, 1993, 9 (6): 454), the total glucosides of paeony are active components extracted from *Paeonia lactiflora* Pall, including paeoniflorin, hydroxyl paeoniflorin, paeonin, albiflorin, benzoyl paeoniflorin and the like, wherein the content of paeoniflorin is more than 90% with respect to the total glycosides. Therefore, the pharmacological effects of the total glucosides of paeony are substantially represented as those of paeoniflorin, and the total glucosides of paeony have effects on the sleep-waking rhythm in rats. In other words, it is only recorded in the prior art that the total glucosides of paeony have effects on the sleep-waking rhythm in rats, but there in no teaching of the efficacy of albiflorin as a monomer compound for the treatment of anxiety and sleeping disorder.

By means of advanced separation and purification technology, the inventor extracts albiflorin, the active component for the treatment of anxiety and sleep disorder, from the root of *Paeonia lactiflora* Pall, with a purity of 50-99%, and the inventor makes pharmacodynamical and pharmacological studies of albiflorin and the corresponding pharmaceutical preparations thereof on the amelioration, treatment of anxiety and sleep disorder (especially the treatment of sleep disorder associated with depression). The results showed that the albiflorin monomer are of clear pharmacological effects for treating anxiety and sleep disorder, significant therapeutic effect, low toxicity and side effects, and high safety. Albiflorin may also make it possible to provide a highly effective and low-toxic medicament for patients suffering from anxiety and sleep disorder. In addition, the comparison between paeoniflorin and albiflorin in the improvement of sleep disorder is also performed. The experimental results showed that albiflorin is notably better than paeoniflorin (which is the main effective component of the total glucosides of peony for treating anxiety and improving sleep disorder) in the improvement of sleep disorder. The traditional view is corrected due to these results.

Health-care food, also called as dietary supplement, is an oral product or preparation containing nutrients, which are uptaken for the purpose of increasing the nutrient in addition to daily meals. It is not a drug, but a kind of food. However, it also differs from those on the table during three meals a day. "Health-care food" falls into the scope of food, but differs from that in the traditional sense. Its function is intended to supply nutrients in addition to daily meals, regulate body functions, and enhance physical fitness.

DESCRIPTION OF THE INVENTION

The object of the present invention is to provide a use of albiflorin or a metabolite of albiflorin in the preparation of a medicament or a health-care food for preventing, ameliorating and/or treating anxiety and sleep disorder. The metabolite of albiflorin is paeonilactone A, or paeonilactone B.

As used herein, the sleep disorder is insomnia, mainly represented as persistent sleep difficulties and early wakening, the sleep disorder also includes that sleep disorder associated with anxiety and/or depression.

The medicament according to the present invention may consist of albiflorin or a metabolites of albiflorin and a pharmaceutically acceptable carrier.

Using methods of the prior art, the medicament can be formulated as a tablet, a capsule, a pill, a powder, a granule, a syrup, a solution, an emulsion, an injection, a spray, an aerosol, or a patch.

Another object of the present invention is to provide a medicament for preventing, ameliorating and/or treating anxiety and sleep disorder, characterized in that the medicament comprises at least one of the following substances: albiflorin, a metabolite of albiflorin, a composition of albiflorin, a herb comprising albiflorin or a herb extract comprising albiflorin. As used herein, the metabolite of albiflorin is paeonilactone A, or paeonilactone B. The content of albiflorin in the herb extract comprising albiflorin is between 6% and 100% by weight. Wherein, the composition of albiflorin can be selected from the group consisting of a pharmaceutically acceptable salt of albiflorin and a solvate of albiflorin.

Another object of the present invention is to provide a health-care food for preventing, ameliorating and/or treating anxiety and sleep disorder, characterized in that the health-care food comprises at least one of the following substances: albiflorin, a metabolite of albiflorin, a composition of albiflorin, a herb comprising albiflorin or a herb extract comprising albiflorin. Wherein, the metabolite of albiflorin is paeonilactone A, or paeonilactone B. The content of albiflorin in the herb extract comprising albiflorin is between 6% and 100%.

Another object of the present invention is to provide a method for preventing, ameliorating and/or treating anxiety and sleep disorder, comprising administering to the patient in need thereof a therapeutically effective amount of albiflorin, a metabolite of albiflorin, a composition of albiflorin, a herb comprising albiflorin or a herb extract comprising albiflorin. Wherein, the content of albiflorin in the herb extract comprising albiflorin is between 6% and 100%.

In other words, the present invention relates to a new use of albiflorin, a metabolites of albiflorin, a composition of albiflorin, a herb comprising albiflorin or a herb extract comprising albiflorin for preventing, ameliorating and/or treating anxiety and sleep disorder, and also relates to a new pharmaceutical use of albiflorin, a pharmaceutically acceptable salt or solvate thereof, or a peony extract comprising an effective amount of albiflorin in the preparation of a medicament or a health-care food for preventing, ameliorating and/or treating anxiety and sleep disorder.

In order to achieve the above objects, the present invention provides a use of albiflorin in the preparation of a medicament or a health-care food for preventing, ameliorating and/or treating anxiety and sleep disorder, especially that sleep disorder associated with depression. As used herein, the sleep disorder refers to insomnia or early awakening characterized by persistent sleep difficulties.

During the screening of natural active components used for treating anxiety and sleep disorder, the inventors found that albiflorin, one of the chemical components present in the extract of traditional Chinese medicine peony, possesses a significant effect, and also found that the two metabolites of albiflorin in the human body, paeonilactone A and paeonilactone B, have medicinal value in the treatment and/or prevention of anxiety and sleep disorder.

Wherein, the "albiflorin" refers to the racemates, the stereoisomers, or the mixtures of stereoisomers mixed in any proportion of albiflorin.

In particular, the two metabolites of albiflorin are paeonilactone A and paeonilactone B.

In particular, the pharmaceutically acceptable carrier is generally recognized to be used for this purpose and used as inactive component of medicament. The summary of pharmaceutically acceptable carriers can be found in "Handbook of pharmaceutical excipients" (Handbook of pharmaceutical excipients, 2nd edition, edited by A. Wade and P. J. Weller; published by the American Pharmaceutical Association, Washington and The Pharmaceutical Press, London, 1994) and other reference books.

Especially, the carrier includes a excipient such as starch, water, and the like; a lubricant such as magnesium stearate, and the like; a disintegrant such as microcrystalline cellulose, and the like; a filler such as lactose, and the like; a binder, such as pregelatinized starch, dextrin, and the like; a sweetener; an antioxidant; a preservative; a flavoring agent; a fragrance; and the like.

Wherein, the medicament is in the form of a tablet, a capsule, a pill, a powder, a granule, a syrup, a solution, an emulsion, an injection, a spray, an aerosol, or patch.

Wherein, the medicament is administered in gastrointestinal route and parenteral route.

In particular, the route of parenteral administration is selected from the group consisting of injection administration, respiratory tract administration, transdermal administration, mucosal administration or cavity administration.

Wherein, the formulation for parenteral administration is selected from the group consisting of an injection, a spray, an aerosol, a paste, and the like.

In particular, the formulation for gastrointestinal administration is selected from the group consisting of a tablet, a capsule, a powder, a granule, a pill, a solution, an emulsion, or a syrup and the like.

Wherein, the content of albiflorin in the herb extract comprising albiflorin is between 6% and 100%, preferably between 10% and 40%, further preferably between 15% and 25%.

In another aspect of the present invention, provided is a use of a composition of albiflorin in the preparation of a medicament or a health-care food for preventing, ameliorating and/or treating anxiety and sleep disorder.

Wherein, the composition of albiflorin is selected from the group consisting of a pharmaceutically acceptable salt of albiflorin and a solvate of albiflorin.

In particular, the pharmaceutically acceptable salt of albiflorin is a physiologically acceptable salt thereof, especially being administered to humans and/or mammals as a medicament.

Wherein, the salt includes a addition salt formed with albiflorin and acid; the solvate of albiflorin is a hydrate of albiflorin.

In particular, the acid is selected from the group consisting of one or more of hydrochloric acid, fumaric acid, maleic acid, citric acid or succinic acid, all these mentioned acids are for the purpose of illustration only, and thus are not limitative of the scope of the present invention.

In another aspect of the present invention, provided is a use of a herb comprising albiflorin or a herb extract comprising albiflorin in the preparation of a medicament or a health-care food for preventing, ameliorating and/or treating anxiety and sleep disorder.

Wherein, the herb comprising albiflorin is selected from the herb Paeonia lactiflora Pall or P. suffrsticosa Andrz, preferably Paeonia lactiflora Pall.

Wherein, the content of albiflorin in the herb extract of comprising albiflorin is between 6% and 100%, preferably between 10% and 40%, further preferably between 15% and 25%.

In another aspect of the present invention, provided is a use of a metabolite of albiflorin in the preparation of a medicament or a health-care food for preventing, ameliorating and/or treating anxiety and sleep disorder.

Wherein, the metabolite of albiflorin is paeonilactone A, or paeonilactone B.

In another aspect of the present invention, provided is a medicament comprising albiflorin for preventing, ameliorating and/or treating anxiety and sleep disorder.

Wherein, the medicament further comprises a pharmaceutically acceptable carrier.

In another aspect of the present invention, provided is a medicament for preventing, ameliorating and/or treating anxiety and sleep disorder, comprising at least one of the following substances: a metabolite of albiflorin, a composition of albiflorin, a herb comprising albiflorin or a herb extract comprising albiflorin.

Wherein, the medicament consists of one of the following substances: a metabolite of albiflorin, a composition of albiflorin, a herb comprising albiflorin or a herb extract comprising albiflorin and a pharmaceutically acceptable carrier.

In particular, wherein, the content of albiflorin in the herb extract comprising albiflorin is between 6% and 100%, preferably between 10% and 40%, further preferably between 15% and 25%.

Wherein, the metabolite of albiflorin is paeonilactone A, or paeonilactone B.

Wherein, the composition of albiflorin is selected from the group consisting of a pharmaceutically acceptable salt and a solvate of albiflorin.

In particular, the pharmaceutically acceptable salt of albiflorin is a physiologically acceptable salt thereof, especially being administered to humans and/or mammals as a medicament.

Wherein, the salt includes an addition salt formed with albiflorin and acid.

In particular, the acid is selected from the group consisting of one or more of hydrochloric acid, fumaric acid, maleic acid, citric acid or succinic acid, all these mentioned acids are for the purpose of illustration only, and thus are not limitative of the scope of the present invention.

Wherein, the solvate of albiflorin is a hydrate of albiflorin.

Wherein, the herb comprising albiflorin is selected from the herb Paeonia lactiflora Pall or P. suffrsticosa Andrz, preferably Paeonia lactiflora Pall.

In particular, the carrier includes a excipient such as starch, water, and the like; a lubricant such as magnesium stearate, and the like; a disintegrant such as microcrystalline cellulose, and the like; a filler such as lactose, and the like; a binder, such as pregelatinized starch, dextrin, and the like; a sweetener; an antioxidant; a preservative; a flavoring agent; a fragrance; and the like.

By means of well known methods in the art, the medicament can be formulated into various dosage forms, such as a tablet, a capsule, a pill, a powder, a granule, a syrup, a solution, an emulsion, an injection, a spray, an aerosol, a patch, and the like.

In another aspect of the present invention, provided is a health-care food for preventing, ameliorating and/or treating anxiety and sleep disorder, comprising one of the following substances: albiflorin, a metabolite of albiflorin, a composition of albiflorin, a herb comprising albiflorin or the herb extract comprising albiflorin.

Wherein, the content of albiflorin in the health-care food is between 6% and 100%, preferably between 10% and 40%, further preferably between 15% and 25%.

The present invention also provides a method for treating anxiety and sleep disorder, comprising administering to the subject in need thereof a therapeutically effective amount of a pharmaceutical composition of albiflorin. The therapeutically effective amount is 0.6-4 mg/kg/d, preferably 1-3.5 mg/kg/d, further preferably 1.2-2 mg/kg/d.

Unless otherwise indicated, the term "therapeutically effective amount" as used herein refers to the amount of medicament intended for having desirable effect; "therapeutically effective amount" can be modified and changed, and finally determined by medical staff, and the factors which should be taken into consideration include the administration routes and formulation properties; body weights, ages and other general conditions of subjects, as well as the natures and severity of the diseases to be treated.

The present invention has the following advantages:

1. The present invention explores the new medicinal value of known compound Albiflorin as well as a pharmaceutically acceptable salt or a solvate thereof, being applied for the treatment of anxiety and the improvement of sleep disorder (by activating 5-HT1A receptor, albiflorin can significantly increase SWS to achieve the efficacy of anti-anxiety and sleep improvement), and prepared into a medicament or a health-care food for preventing, ameliorating and/or treating sleep disorder associated with depression, and thereby opening up a new field for the application of the herb *Paeonia lactiflora* Pall and the like.

2. A series of experimental studies of the present invention show that Albiflorin has significant effect on the prevention and treatment of anxiety and sleep disorder, and is the main active component for the treatment of anxiety and sleep disorder (especially that sleep disorder associated with depression) in *Paeonia lactiflora* Pall and the extract of *Paeonia lactiflora* Pall. This discovery corrects the traditional view that paeoniflorin is the main active component of total glucosides of paeony for the treatment of anxiety and sleep disorder.

3. Albiflorin according to the present invention is of clear action mechanism for treating anxiety and sleep disorder, and has significant therapeutic effect, low toxicity and side effects, and high safety, which could be administered for a long time and has a high druggability and a good prospect in pharmaceutical application.

4. The product of the present invention has sufficient and low-cost sources of raw materials, high clinical safety and simple preparing process. It can be formulated into various dosage forms, administered in a small dose, easily applied, and thus readily promoted.

5. According to the present invention, the active component of Albiflorin can be not only independently prepared into the medicaments for preventing and treating anxiety and sleep disorder, but also prepared into multi-target compound medicaments for the treatment of anxiety and sleep disorder, in combination with other active components (for example, paeoniflorin, glycyrrhizic acid, Schisandrin B, and the like).

Preferred Embodiments

The present invention will now be further described by reference to the following examples. But these examples are for illustrative purposes only, and thus not to be construed as a limitation of the scope of the present invention. In the following examples, the experimental methods without specifically indicated conditions are often in accordance with conventional conditions, or in accordance with the conditions recommended by the manufacturers.

The beneficial effects of medicaments of the present invention will be further described by means of the following experimental examples; these experimental examples include the pharmacodynamic tests of the medicaments of the present invention.

EXAMPLE 1

100 g of albiflorin with a purity of 96.77% was added to 50 g of starch and 10 g of starch silica, mixed well and then directly filled into hard gelatin capsules, to obtain the capsules comprising 40 mg of albiflorin per capsule.

EXAMPLE 2

100 g of albiflorin with a purity of 92% was ground and sifted through a 100 mesh sieve, and then mixed well with 100 g of starch which was sifted through a 100 mesh sieve. An appropriate amount of starch slurry was added thereinto under homogeneous stiffing, sifted through a 16 mesh iron wire sieve, dried below 60° C., and then granulated. An appropriate amount of magnesium stearate was added thereinto, mixed well and placed into a tablet press to obtain the tablets comprising 30 mg of albiflorin per tablet.

EXAMPLE 3

10 g of albiflorin with a purity of 98.5% and 90 g of sodium chloride was added to water for injection and dissolved under stiffing. When adding water for injection up to 1000 ml, the solution was then filtered with 0.22 µm microporous membrane filter, subdivided and sealed, and sterilized to obtain an infusion formulation of albiflorin and sodium chloride.

EXAMPLE 4

100 g of the extract of *Paeonia lactiflora* Pall with an albiflorin content of 16% was ground to 200 mesh, added into 100 g of swollen sodium carboxymethyl cellulose (CMC), and homogeneously stirred. Distilled water was added thereinto until 10 L, and stirred to obtain a suspension, comprising 10 mg of albiflorin per milliliter of suspension.

EXAMPLE 5

Effect of Albiflorin on Mice in Light-dark Box Test (Anti-anxiety Test)

5.1 Experimental Materials and Methods 5.1.1 Drugs

Albiflorin (96.77%), supplied by Beijing Wonner Biotech Co., Ltd. (Beijing, China). Diazepam, produced by Jin-Hui Amino Acid Co., Ltd. (Tianjin, China).

5.1.2 Animals

KM mice, male, with the weight of 24-26 g, Class 2, supplied by the Experimental Animal Center, Peking University Health Science Center.

5.1.3 Equipments

Homemade light-dark box.

5.1.4 Methods 5.1.4.1 Grouping and Administration Methods of Animals

Mice were randomly divided into 5 groups, i.e. high-dose group (14 mg/kg/d), medium-dose group (7 mg/kg/d), low-dose group (3.5 mg/kg/d) of Albiflorin, diazepam group (2.5 mg/kg/d), NS group. Gavage administration was performed once a day, for consecutive 7 days. During the administration, animals had free access to feed and water. The test was carried out 1 hour after the administration on Day 8.

5.1.4.2 Light-Dark Box Tests in Mice

Within the light-dark box (44 cm×21 cm×21 cm), the dark box accounts for one third thereof, with a cover on the top; while the light box accounts for two thirds thereof, providing illumination brightness; and there is a hole between the two boxes for animal to pass through. In the test, mice were placed in the center of the light box, back to the dark box, and then observed. The times of entering into the dark box followed by returning to the light box in mice were counted, as an index for the assession of anti-anxiety effect of a drug.

5.1.5 Statistical Analysis

The data were expressed as $\overline{X}\pm SD$, and the experimental results were analyzed by one-way ANOVA, using SPSS 11.5 statistical software.

5.2 Results

Effect of albiflorin on the times of passing through box in mice in light-dark box test are shown in Table 1. All the high-, medium- and low-dose groups of albiflorin as well as diazepam group can significantly increase the times of returning from the dark box back to the light box in mice, and have statistical significance in comparison to NS group.

TABLE 1

Effect of albiflorin on the times of passing through box in mice in the light-dark box test

| | Number of Animal | Dose (mg/kg/d) | Times of Returning from Dark Box back to Light Box |
|---|---|---|---|
| high-dose albiflorin: | 10 | 14 mg/kg/d | 12.1 ± 3.51** |
| medium-dose albiflorin: | 10 | 7 mg/kg/d | 13.4 ± 3.23** |
| low-dose albiflorin: | 10 | 3.5 mg/kg/d | 10.6 ± 3.42* |
| diazepam | 10 | 2.5 mg/kg/d | 13.6 ± 3.35** |
| NS | 10 | — | 6.9 ± 3.74 |

Note:
*P < 0.05,
**P < 0.01, compared to NS group.

5.3 Conclusions

The light-dark box test is an experimental model for anti-anxiety study, which is designed on the basis of congenital aversion to hard light and spontaneous exploratory behavior in new environment of murine. All drugs having anti-anxiety effect can increase the speed of passing through box and the residence time in light box of animal; however, non anti-anxiety agents do not have such an effect. The results of light-dark box test employed in the present invention showed that all the high-, medium- and low-dose groups of albiflorin as well as diazepam group can significantly increase the times of returning from the dark box back to the light box in mice, and have statistical significance in comparison to NS group (P<0.01, P<0.05). The experimental results showed that albiflorin had anti-anxiety effect.

EXAMPLE 6

Effect of Albiflorin on Sleep Rhythms in Rats 6.1 Reagents and Materials 6.1.1 Materials 6.1.1.1 Drugs Albiflorin (98.3%), supplied by Beijing Wonner Biotech Co., Ltd. It is dissolved in NS and prepared into the required concentration prior to use.

6.1.1.2 Animals

Male SD rats, n=30, with the weight of 200-250 g, 3-4 months old, supplied by Vital River Experimental Animal Center.

6.1.1.3 Equipments

NISSAN RM-6000 type 8-path physiological recorder, domestic JIANGWAN I type C general stereotactic instrument.

6.2 Methods 6.2.1 Installation of Recording Electrodes in Rats

The rat was anesthetized with sodium pentobarbital (35 mg/kg, ip), fixed in JIANGWAN I type stereotactic instrument, shorn on the head and disinfected. A skin incision was made to expose the skull, separate the periosteum, and insert a gold-plated screw electrode into parietal cortex and occipital cortex, respectively, making them contact with dura mater in order to record cortical electroencephalogram (EEO) in rat. In addition, a pair of gold-plated bare wire electrodes were inserted at the left and right sides of pre-muscle or neck muscle respectively, for recording electromyogram (EMG). After the embedment, the electrodes were fixed with self-curing denture powder, and welded to a micro socket for the use of recording.

6.2.2 Experimental Records and Analysis

The rats embedded with recording electrodes were individually housed in a homemade circular plexiglass cage, and applied to the experiment after being left to naturally recover for 1 week. Before the experiment, the animals were placed in a shielded room without noise interference to acclimate for 24 h, keeping a 12/12 h rhythmic change of light and dark. Room temperature was 22±2° C., humidity was 60±10, the signals of EEG and EMG were received by 8-path physiological recorder and synchronously graphed on recording paper (pepar speed: 10 mm/s), for consecutive 6 h. The result of observation was recorded: by means of visual method, it is divided into 3 phases, waking, slow-wave sleep and paradoxical sleep (PS), taking 60 s for a period to calculate Episode frequency and Episode during of each phase.

6.3 Results 30 rats embedded with electrodes were grouped and administered according to the Table. The normal polysomnograph were graphed twice prior to administration (one graphy for each day, and consecutive 6 h for one graphy), and the mean value thereof was taken as a normal basic control. The results in Table 2 showed that after the consecutive administration of two doses of albiflorin for one day, there is no significant effect on each sleep phase of rats;

after the consecutive administration for five days, the low-dose group of albiflorin (7 mg/kg) exhibited a trend of prolonged SWS phase; after the consecutive administration for seven days, this low-dose group could significantly shorten the waking time of rats, and prolong the time of slow wave sleep (SWS). Compared with that prior to administration, the SWS phase was prolonged by an average of 23.26% (P<0.05), while PS was not significantly affected.

TABLE 2

Effect of albiflorin on the sleep period in rats
(for consecutive 6 h) (x ± s)

| Drug | Dose (mg/kg/d) | n | Sleep Phase | Prior to Administration (%) | Day 1 | Day 3 | Day 5 | Day 7 |
|---|---|---|---|---|---|---|---|---|
| NS | — | 10 | SWS | 51.7 ± 4.3 | 51.2 ± 5.5 | 52.5 ± 6.6 | 54.2 ± 5.4 | 54.2 ± 4.1 |
|  |  |  | PS | 7.2 ± 1.1 | 7.5 ± 1.6 | 7.3 ± 1.4 | 8.1 ± 2.0 | 7.3 ± 1.4 |
|  |  |  | Waking | 41.8 ± 4.9 | 40.8 ± 5.0 | 39.6 ± 5.5 | 37.6 ± 6.1 | 38.7 ± 4.0 |
| Albiflorin | 14 | 10 | SWS | 50.4 ± 4.6 | 52.1 ± 4.8 | 53.3 ± 5.1 | 54.5 ± 5.5 | 55.1 ± 3.2 |
|  |  |  | PS | 6.9 ± 0.8 | 7.0 ± 1.2 | 7.3 ± 1.3 | 7.6 ± 1.5 | 6.1 ± 1.2 |
|  |  |  | Waking | 37.1 ± 3.3 | 36.5 ± 6.5 | 36.7 ± 7.0 | 30.4 ± 7.5 | 36.4 ± 4.5 |
|  | 7 | 10 | SWS | 54.6 ± 3.4 | 55.9 ± 6.7 | 56.3 ± 5.9 | 61.8 ± 6.1 | 67.3 ± 3.6* |
|  |  |  | PS | 8.1 ± 0.8 | 7.7 ± 1.8 | 7.2 ± 1.3 | 8.0 ± 1.5 | 7.2 ± 1.1 |
|  |  |  | Waking | 40.6 ± 4.8 | 41.2 ± 5.3 | 40.1 ± 5.6 | 37.6 ± 4.5 | 38.6 ± 4.2 |

Note:
compared with that prior to administration, *P < 0.05

6.4 Discussions

The experimental results showed that:

1. Albiflorin (7 mg/kg, ig×7 d) could change the distribution of various sleep phases in normal rats, exhibiting that waking time of rats is shortened, and SWS time was significantly prolonged.

2. The action mechanism of albiflorin effect on sleep may be associated with the stimulation of 5-HTA1 receptor in postsynaptic membrane of central nerve, and this issue needs to be further studied.

EXAMPLE 7

Study on Sleep-improving Effects of Paeoniflorin and Albiflorin 7.1 Grouping and Administration of Aminals 7.1.1 Grouping of Aminals 140 ICR mice (15-17 g, male, purchased from Institute of Laboratory Animal Sciences, CAMS & PUMC) were randomly divided into 10 groups (14 mice per group) as follows: paeoniflorin group at a dose of 100 mg/kg, paeoniflorin group at a dose of 50 mg/kg, paeoniflorin group at a dose of 25 mg/kg, paeoniflorin group at a dose of 12.5 mg/kg, albiflorin group at a dose of 28 mg/kg, albiflorin group at a dose of 14 mg/kg, albiflorin group at a dose of 7 mg/kg, normal saline control group, high-dose group of doxepin as a positive drug (25 mg/kg), and low-dose group of doxepin as a positive drug (1 mg/kg).

7.1.2 Reagents

Albiflorin and paeoniflorin (supplied by Beijing Wonner Biotech Co., Ltd.); Doxepin Hydrochloride (prepared by Hengsheng Pharmaceutical Co., Ltd., Beijing, China, purchased from Tiantan Hospital); Diazepam (prepared by Yimin Pharmaceutical Co., Ltd., Beijing, China, purchased from Tiantan Hospital); Pentobarbital Sodium (purchased from Sinopharm Chemical Reagent Beijing Co., Ltd.).

7.2 Experimental Methods 7.2.1 Evaluation Criteria of Sleep Latency, Sleep Duration and Sleep Rate If the mice were kept in a supine position for more than 1 min, it would be considered that the righting reflex was disappeared in mice. After spontaneously rolling over, the mice were immediately placed in a supine position. If the mice could roll over within 1 min, it would be considered that the righting reflex was recovered. The time of the righting reflex being disappeared and recovered in mice were recorded. The period from the mice being intraperitoneally injected with pentobarbital sodium until the righting reflex being disappeared in mice was recorded as sleep latency. The period from the righting reflex being disappeared in mice until the righting reflex being recovered in mice was recorded as sleep duration. The sleep duration of more than 5 min in mice was considered as being asleep.

7.2.2 Determination of Minimum Suprathreshold Dose and Maximum Subthreshold Dose of Pentobarbital Sodium 4 mice were randomly selected, intraperitoneally injected with pentobarbital sodium (45 mg/kg, 0.1 ml/10 g), and observed for the righting reflex being disappeared and recovered in mice within 15 min, the evaluation criteria can be found in Section 7.2.1. According to the experimental results, the doses of pentobarbital sodium were further adjusted to 51 mg/kg, 40 mg/kg, 35 mg/kg, and 38 mg/kg. The righting reflex being disappeared and recovered within 15 min in mice were observed to preliminarily confirm that the maximum subthreshold dose of pentobarbital sodium was 35 mg/kg, the minimum suprathreshold dose was 51 mg/kg. According to the same experimental methods, the number of mice was further increased, and the righting reflex being disappeared and recovered within 15 min in mice were observed. The dose of pentobarbital sodium making 100% of mice in each group sleep was the suprathreshold dose, while the dose making more than 90% of mice in each group not sleep was the subthreshold dose of pentobarbital sodium.

7.2.3 The Sleep-prolonging Test of Pentobarbital Sodium at the Suprathreshold Dose The mice were administered with drugs for consecutive 10 days. 1 h after the last administration, the mice were intraperitoneally injected with the suprathreshold dose of pentobarbital sodium (51 mg/kg, 0.1 ml/10 g). The righting reflex being disappeared and recovered in mice were observed, and the time of the righting reflex being disappeared and recovered in mice were recorded. The evaluation criteria of sleep latency, sleep duration and sleep rate were the same as those in Section 7.2.1.

7.2.4 The Sleeping-inducing Test of Pentobarbital Sodium at the Subthreshold Dose The mice were administered with drugs for consecutive 14 days. 1 h after the last administration, the mice were intraperitoneally injected with the subthreshold dose of pentobarbital sodium (35 mg/kg, 0.1 ml/10 g). The righting reflex being disappeared and recovered in mice were observed, and the time of the righting reflex being disappeared and recovered in mice were recorded. The evaluation criteria of sleep latency, sleep duration and sleep rate were the same as those in Section 7.2.1.

7.3 Experimental Results

TABLE 3

Effects of paeoniflorin and albiflorin on the sleep-prolonging of pentobarbital sodium at the suprathreshold dose (10 days after administration)

| Groups | Sleep Latency (min) | Sleep Duration (min) |
|---|---|---|
| Albiflorin (28 mg/kg) | 13.17 ± 23.54 | 84.14 ± 20.72 |
| Albiflorin (14 mg/kg) | 5.89 ± 3.12 | 87.66 ± 32.04* |
| Albiflorin (7 mg/kg) | 4.45 ± 1.89 | 97.46 ± 11.81** |
| Paeoniflorin (100 mg/kg) | 28.10 ± 44.63 | 72.98 ± 20.83 |
| Paeoniflorin (50 mg/kg) | 5.17 ± 1.37 | 73.70 ± 27.88 |
| Paeoniflorin (25 mg/kg) | 4.96 ± 2.18 | 68.64 ± 19.23 |
| Paeoniflorin (12.5 mg/kg) | 4.11 ± 1.52 | 74.57 ± 13.02 |
| Doxepin (1 mg/kg) | 4.38 ± 1.60 | 74.91 ± 16.55 |
| Doxepin (25 mg/kg) | 4.72 ± 2.40 | 63.60 ± 12.09 |
| normal saline control | 6.05 ± 4.78 | 69.83 ± 24.24 |

The data were expressed as Means ± S.D.,
ONE-WAY ANOVA test, *P < 0.05, **P < 0.01

TABLE 4

Effects of paeoniflorin and albiflorin on the sleeping-inducing of pentobarbital sodium at the subthreshold dose (14 days after administration)

| Groups | Number of Mice/Group | Number of Sleeping Mice/Group | Sleep Rate |
|---|---|---|---|
| Albiflorin (28 mg/kg) | 13 | 0 | 0/13 |
| Albiflorin (14 mg/kg) | 13 | 8 | 8/13* |
| Albiflorin (7 mg/kg) | 13 | 10 | 10/13* |
| Paeoniflorin (100 mg/kg) | 11 | 3 | 3/11 |
| Paeoniflorin (50 mg/kg) | 12 | 5 | 5/12 |
| Paeoniflorin (25 mg/kg) | 12 | 4 | 1/3 |
| Paeoniflorin (12.5 mg/kg) | 12 | 2 | 2/13 |
| Doxepin (1 mg/kg) | 12 | 1 | 1/12 |
| Diazepam (2 mg/kg) | 13 | 12 | 12/13* |
| normal saline control | 13 | 2 | 2/13 |

The data were expressed as Means ± S.D.,
Chi-square test, *P < 0.05, **P < 0.01

TABLE 5

Effects of paeoniflorin and albiflorin on spontaneous actions in mice (14 days after administration)

| Groups | Times of Spontaneous Action |
|---|---|
| Albiflorin (28 mg/kg) | 476.78 ± 113.78 |
| Albiflorin (14 mg/kg) | 393.28 ± 107.73* |
| Albiflorin (7 mg/kg) | 342.64 ± 133.38** |
| Paeoniflorin (100 mg/kg) | 434.45 ± 76.43 |
| Paeoniflorin (50 mg/kg) | 503.00 ± 137.04 |
| Paeoniflorin (25 mg/kg) | 468.71 ± 73.56 |
| Paeoniflorin (12.5 mg/kg) | 456.71 ± 93.95 |
| Doxepin (1 mg/kg) | 420.50 ± 110.28 |
| Diazepam (2 mg/kg) | 301.85 ± 103.11** |
| normal saline control | 482.46 ± 74.15 |

The data were expressed as Means ± S.D.,
ONE-WAY ANOVA test, *P < 0.05, **P < 0.01

7.4 Experimental Results

After the Administration was performed for consecutive 10 days, albiflorin group (14 mg/kg) and albiflorin group (7 mg/kg) could significantly prolong the sleep time at the suprathreshold dose of pentobarbital sodium; after the Administration was performed for consecutive 14 days, albiflorin group (14 mg/kg), albiflorin group (7 mg/kg) and positive drug group of diazepam could significantly increase the sleep rate at the subthreshold dose of pentobarbital sodium, and decrease the times of spontaneous action. The results suggested that albiflorin (14 mg/kg) and albiflorin (7 mg/kg) may have hypnotic effect to a certain extent.

EXAMPLE 8

Effect of *Paeonia Lactiflora* Pall Extract (Comprising 16% of Albiflorin) on the mRNA Expression of 5-HT1A Receptor in Chronic Stress Rats 8.1 Experimental Materials 8.1.1 Experimental Drugs The test drug, *Paeonia lactiflora* Pall extract (comprising 16% albiflorin), supplied by Beijing Wonner Biotech Co., Ltd. Positive drug, fluoxetine hydrochloride (fluoxetine, Prozac), supplied by Eli Lilly & Company (LLY), Suzhou, China (Lot Number: Chinese Drug Approval Number: J20030017).

8.1.2 Experimental Animals

Wistar rats, Male, with the weight of 220 g-240 g, supplied by Beijing Vital River Experimental Animal Center; all animals were purchased one week in advance, and routinely fed.

8.1.3 Equipments and Reagents

Universal 32R low-temperature high-speed centrifuge (Hettich, Germany); CD3192 electric constant-temperature water bath (Charcoal-in-Snow Thermostat Technology Co., Ltd., Hangzhou, China); SPECTRAmax190 (Molecular Devices, USA); PTC-200 PCR instrument (MJ Research, USA); DYY-8C electrophoresis meter (Liuyi Instrument Factory, Beijing, China); ChampChemi X Type chemiluminescent gel image analysis system (Saizhi Chuangye Technology Co., Ltd., Beijing, China); TRIzol (Invitrogen), DEPC (Amresco), RevertAid First Strand cDNA Synthesis Kit (Fermentas).

8.2 Methods

8.2.1 Grouping and Administration

After having free access to food and being deprived water for 24 h, 72 normal rats were administered with 1% sucrose aqueous solution, and measured the consumption within 1 h. According to the consumption of sucrose aqueous solution, the rats were randomly divided into six groups, 12 mice per group, i.e. normal control group, model group, positive drug Prozac group (2.5 mg/kg/d), high-dose group (70 mg/kg/d, comprising 11.2 mg of albiflorin), medium-dose group (35 mg/kg/d, comprising 5.6 mg of albiflorin), and low-dose group (17.5 mg/kg/d, comprising 2.8 mg of albiflorin) of *Paeonia lactiflora* Pall extract. When being modeled, the rats were simultaneously administered with drugs, once a day, for consecutive 21 days. The rats in various groups were administered at a dose of 1.0 ml/100 g with respect to body weight, and weighed once a week.

8.2.2 Modeling

The rats in control group were fed in a group-breeding way, while the rats in treatment group and model group were separately fed per cage. The rats in treatment group and model group were randomly subjected to various stresses for 21 days, including swimming in the ice water at 4° C. (5 min), drying at 45° C. (5 min), tail-clipping (1 min), wet feeding (wet bedding), reversed day and night (24 h), fasting (24 h), water deprivation (24 h) and the like.

8.2.3 RT-PCR Tests

8.2.3.1 Sampling

After the chronic stress was completed, the rat was immediately decapitated. The brain was taken out and placed on the ice. The hippocampus was rapidly separated, and stored at a low temperature of −70° C. for later use.

8.2.3.2 Extraction of Total RNAs

According to the instruction of TRIzol reagent, the total RNAs were extracted by one-step guanidine-isothiocyanate method. The integrity of the extracted total RNAs was confirmed by 0.9% agarose gel electrophoresis, and the content and purity of RNA were determined by UV spectrophotometer.

8.2.3.3 RT-PCR

To the total RNAs as sample, Oligo (dT) and M-MLV reverse transcriptase were added. A 25 μl of reaction system was reacted at 42° C. for 60 min to synthesize the first strand of cDNA. After that, it is heated at 94° C. for 2 min to inactivate the reverse transcriptase. According to the instruction of PCR, in a 25 μl system, 2 μl of reactant mentioned above was taken. 12.5 μl of PCRMix was added thereinto, and 2 μl of the following two primers were added thereinto, respectively. The sequences of 5-HT1A-R primer are: upstream 5' CCC AGC GAG TCA GGA TCT AAC 3', downstream 5' GAT TGA GCA GGG AGT TGG AGT 3', with an amplification length of 268 bp. The sequences of β-actin primer are: upstream 5' CAT CCT GCG TCT GGA CCT 3', downstream 5' CAC ACA GAG TAC TTG CGC TCA 3', with an amplification length of 498 bp. The reaction condition of PCR was as follows: denaturation at 95° C. for 5 min. 95° C., for 30 seconds; 58° C., for 30 seconds; 72° C., for 30 seconds; 25 cycles in all.

8.2.3.4 Semi-Quantitative Analysis of the Amplified Products

30 μl of 5-HT1A-R-amplified product and 10 μl of Actin-amplified product were mixed, and then subjected to 1.5% agarose gel electrophoresis. The electrophoresis was performed at 100V for 30 min. After the image acquisition by means of chemiluminescent gel image analysis system, the gray scanning of bands was performed by ChampGel gel image processing and analysis software. The ratio of IOD5-HTR/IODActin was the relative quantification of the amplified products, and the intergroup comparisons were carried out.

8.2.4 Statistical Analysis

Experimental data were expressed as mean±standard deviation ($\bar{x}\pm s$). The intergroup comparison was carried out by one-way ANOVA test, using SPSS13.0 statistical software, 0.05 and 0.01 were regarded as significance level.

8.3 Experimental Results

Effect of Paeonia lactiflora Pall extract (comprising 16% of albiflorin) on the mRNA expression of 5-HT1A receptor in chronic stress rats were shown as follows: after the administration for consecutive 21 days, compared with normal control group, the level of mRNA expression of 5-HT1A receptor was decreased in the rats of model group ($P<0.05$); compared with model group, the levels of mRNA expression of 5-HT1A receptor were increased in the rats of high-dose group and medium-dose group of *Paeonia lactiflora* Pall extract as well as positive drug Prozac group ($P<0.05$); See Table 6.

TABLE 6

Effect of *Paeonia lactiflora* Pall extract (comprising 16% of albiflorin) on the mRNA expression of 5-HT1A receptor in chronic stress rats

| Groups | Dose (mg/kg) | Number of Sample | mRNA expression of 5-HT1A receptor |
|---|---|---|---|
| Normal Control | — | 6 | 0.70 ± 0.16* |
| Model | — | 6 | 0.31 ± 0.07 |
| Positive Drug | 2.5 mg/kg/d | 6 | 0.63 ± 0.21* |
| Low-Dose of *Paeonia lactiflora* Pall extract | 17.5 mg/kg/d | 6 | 0.39 ± 0.23 |
| Medium-Dose of *Paeonia lactiflora* Pall extract | 35 mg/kg/d | 6 | 0.63 ± 0.11* |
| High-Dose of *Paeonia lactiflora* Pall extract | 70 mg/kg/d | 6 | 0.63 ± 0.14* |

Compared with model group, *$P < 0.05$, **$P < 0.01$

8.4 Discussions

The hippocampus is an important limbic system structure involved in the regulation of affection, cognition, and behavior, being rich in postsynaptic membrane 5-HT1A receptors. The present experiment employs a chronic and unpredictable stress-induced depression model in rat to simulate the chronic and low-level stress-induced depression in human, in order to study the 5-HT1AR in hippocampus and explore the biochemical cause of depression at the receptor level.

The 5-HT1AR, comprising 421 amino acids, belongs to G protein-coupled receptor family. Human 5-HT1AR gene is located in the q11.2-q13 region of chromosome 5. Presynaptic membrane 5-HT1AR autoreceptor is mainly located in the 5-HT neuron cell body dendrites of dorsal raphe nucleus in the brainstem, the activation of which inhibits the electrical activity of the 5-HT neurons, and reduces the release of 5-HT neurotransmitter in prefrontal cortex. Postsynaptic membrane 5-HT1AR is mainly located in hippocampus, amygdala, prefrontal cortex, regulating the release of 5-HT. The main transduction mechanism of 5-HT1AR is G protein-coupled transduction inhibiting adenylate cyclase (AC). Although there are many reports concerning 5-HT1AR and depression, but there is no uniform understanding. There is a group of basic studies reporting that acute and chronic unpredictable stresses increase the glucocorticoid in plasma, and down-regulate the binding of 5-HT1AR and the mRNA levels of 5-HT1AR. When using [11C] WAY-100635PET method to determine the 5-HT1AR in brain, Sargent found that the bindings of 5-HT1AR in prefrontal cortex, temporal cortex, and limbic cortex of patients having severe depression were generally decreased. Stockmeier et al. reported that the [3H] 8-OH-DPAT-bound presynaptic membrane 5-HT1AR was significantly increased in the raphe nuclei area of brainstem of suicidal patient having depression. These evidences are used to support the view of "when suffering from the depression, the presynaptic membrane 5-HT1AR autoreceptor is hypersensitive, while the postsynaptic membrane 5-HT1AR is hyposensitive". Tricyclic antidepressants play an antidepressant effect by increasing the sensitivity of postsynaptic membrane 5-HT1AR. 5-HT reuptake inhibitor (SSRI) desensitizes the presynaptic membrane 5-HT1AR autoreceptor, thereby plays an antidepressant effect. 5-HT1AR autoreceptor antagonist can improve the antidepressant effect of SSRI, and significantly shorten the onset of antidepressant action. Buspirone can selectively excite the postsynaptic membrane 5-HT1AR, having a significant antidepressant effect.

The experimental results showed that the levels of mRNA expression of 5-HT1A receptor were decreased in hippocampus of rat model of stress-induced depression, which is consistent with recent foreign reports, suggested that hippocampal 5-HT1A receptor was closely related to the occurrence of chronic stress-induced depression. The test drug, *Paeonia lactiflora* Pall extract (comprising 16% of albiflorin) could work against the decrease in the mRNA expression of 5-HT1A receptor in hippocampus, which was caused by chronic stress. The results suggested that the effects of antidepressant, anti-anxiety and sleep-improvement by prolonging SWS might be associated with the up-regulation of 5-HT1A receptor in hippocampus.

What is claimed is:

1. A method for ameliorating and/or treating insomnia comprising administering to a patient in need thereof a medicament consisting of a therapeutically effect amount of albiflorin, pharmaceutically acceptable salts or a medicament of albiflorin, and a pharmaceutically acceptable carrier.

2. The method according to claim 1, wherein said metabolite of albiflorin is paeonilactone A or paeonilactone B.

3. The method according to claim 1, wherein said medicament is in the form of a tablet, a capsule, a pill, a powder, a granule, a syrup, a solution, an emulsion, an injection, a spray, an aerosol or patch.

4. The method according to claim 1, wherein the insomnia is represented as persistent difficulties and early wakening.

* * * * *